US00PP25761P3

(12) United States Plant Patent
Raymer et al.

(10) Patent No.: US PP25,761 P3
(45) Date of Patent: Jul. 28, 2015

(54) **SEASHORE *PASPALUM* PLANT NAMED 'UGA 31'**

(50) Latin Name: *Paspalum vaginatum*
Varietal Denomination: UGA 31

(71) Applicant: University of Georgia Research Foundation, Inc., Athens, GA (US)

(72) Inventors: Paul L. Raymer, Milner, GA (US); Leon L. Burpee, Athens, GA (US); Robert N. Carrow, Athens, GA (US); Brian M. Schwartz, Athens, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 170 days.

(21) Appl. No.: 13/986,795

(22) Filed: Jun. 4, 2013

(65) Prior Publication Data

US 2014/0359910 P1 Dec. 4, 2014

(51) Int. Cl.
*A01H 5/00* (2006.01)

(52) U.S. Cl.
USPC ..... Plt./387

(58) Field of Classification Search
USPC ..... Plt./387
See application file for complete search history.

(56) References Cited

PUBLICATIONS

Arkansas Turfgrass Report 2008 pp. 60-63. 2007.*

* cited by examiner

*Primary Examiner* — Annette Para
(74) *Attorney, Agent, or Firm* — Klarquist Sparkman, LLP

(57) ABSTRACT

A new and distinct vegetatively reproduced cultivar of seashore *paspalum, Paspalum vaginatum,* which is characterized by a combination of excellent green turf color, non-dwarf rapidly spreading growth habit, good salt tolerance, its ability to maintain high turf density and quality at a range of mowing heights, and the ability to maintain turf quality and to resist leaf firing during periods of short term drought.

5 Drawing Sheets

Botanical classification: *Paspalum vaginatum* O. Swartz.
Varietal denomination: 'UGA 31'.

BACKGROUND OF THE INVENTION

The present invention comprises a new and distinct cultivar of *Paspalum vaginatum,* commonly known as seashore *paspalum,* and hereafter referred to by the varietal denomination 'UGA 31'

*Paspalum vaginatum* is a grass in the Panicoideae subfamily that inherently colonizes saline ecosystems, e.g. along sea coasts and on brackish sands. It is an ecologically aggressive, littoral warm-season perennial grass species varying in leaf texture from very coarse wild ecotypes to finer-leaf textured ecotypes for use in recreational turf. It produces both rhizomes and stolons and can tolerate waterlogged conditions and periodic meso-saline flooding. The grass occurs in the wild in both hemispheres. In the Americas, potential turf ecotypes are found almost exclusively along the Atlantic coastline in marshy, brackish ecosystems while the wild, native types can be found in coastal venues along the Atlantic, Gulf of Mexico and Pacific exposed regions. Generally, *P. vaginatum* is a self-incompatible, diploid species with 20 chromosomes. *P. vaginatum* has been introduced into salt-affected areas as the need for forages, land reclamation and recreational turf have increased. An increase in golf course developments placed on coastal venues or with problems associated with salinity are becoming more prevalent in managed turfgrass. The trend for use of more salt-laden irrigation waters on turfgrass sites is expected to continue to rise and to further increase industry demands for salt tolerant grasses specifically adapted for course-wide use on roughs, fairways, tees, and greens.

'UGA31' originated from a single seed arising from the open-pollinated cross (SIPV-2×unknown). This cross was made in a greenhouse at Griffin, Ga. in 2003 by Dr. Paul Raymer. The female parent (SIPV-2) (unpatented) was allowed to flower in close proximity to 34 other breeding lines of seashore *paspalum* in an open-pollinated crossing block. Since seashore *paspalum* is self-incompatible, the male parent is presumed to be one of the 34 other lines in the polycross. The single plant was germinated from seed in the laboratory and was established in a greenhouse.

The 'UGA 31' seedling was visually screened for acceptable turf quality and for salt tolerance and transplanted into a nursery field for initial turf evaluation in the spring of 2004. This plant was evaluated beginning in June 2004 in an unreplicated field plot mowed at a 1.5 inch height of cut (h.o.c.). The new plant was selected in the fall of 2004 based on turf superior quality, density, and color. The new plant was asexually propagated in 2004 by vegetative propagation in Griffin, Ga. This new plant can be asexually propagated by sprigs, plugs or sod. 'UGA 31' was then evaluated for salt tolerance in a replicated greenhouse study in 2005. 'UGA 31' was then included in a replicated preliminary turf field evaluation (0.5-inch height of cut) at Griffin, Ga., established in June, 2005. Late in 2006, 'UGA 31' was selected as a cultivar with superior turf quality traits based on its performance in the 2005 preliminary trial. The new 'UGA 31' plant was clonally increased for inclusion in advanced turf variety trials at Tifton, Ga. as well as 2007 National Turfgrass Evaluation Trials for Seashore *Paspalum* at eight locations. In 2008, 'UGA31' was one of twelve entries included in a greens trial (0.18 to 0.25 inch height of cut) at Griffin, Ga. 'UGA31' was also included in lawn management trial established at Tifton, Ga., in 2009. 'UGA 31' was evaluated again for salt tolerance in 2010. 'UGA 31' has been evaluated for drought tolerance in both greenhouse and field studies and for disease resistance in both growth chamber and field studies.

SUMMARY OF THE INVENTION

The following characteristics have been consistently found in successive asexually propagated 'UGA 31' plants, and, to the best knowledge of the inventors, the combination of these characteristics of 'UGA31' make it unique as a new and distinct cultivar:

1) An upright non-dwarf growth habit that tolerates a wide range of mowing heights, yet maintains excellent turf density and quality. This combination of traits makes 'UGA31' very useful as a grass that can be used in various applications, such as on all parts of a golf course, including greens, tees, fairways, and roughs.
2) Excellent turf color that is aesthetically pleasing and retains color even during moderate periods of cool temperature. This trait enhances the attractiveness of the grass when used on golf courses and, in some environments, may eliminate the need for overseeding with cool season grasses.
3) The ability to maintain turf quality and resist leaf firing during periods of short-term drought. This reduces the frequency of irrigation needed to maintain turf quality and may significantly reduce water usage in many environments.

COMPARISON TO OTHER VARIETIES

'UGA31' has been compared primarily to 'SI 98' (U.S. Plant Pat. No. 18,869), a variety recently developed for course-wide use in the golf industry, and which is believed by the inventors to be the most similar to 'UGA 31'. Comparative evaluations of the grasses grown in the greenhouse and in field research plots at Griffin, Ga. and other US locations showed that 'UGA31' consistently differed from 'SI 98' in the following characteristics:

1) Turf quality and density. (Data from tables 1, 2, 3). 'UGA31' produces very high quality medium to fine textured turf over a range of mowing heights.
2) Turf color. (Data from tables 1 and 2).
3) Better dollar spot (*Sclerotinia homoeocarpa*) resistance. (Data from tables 1 and 2).
4) Better drought tolerance. (Data from tables 8 and 9).
5) 'UGA31' shows many significant morphological differences from 'SI 98' (data from table 11). The peduncle diameter of flowering tillers in 'UGA31' is smaller than in 'SI 98' and the length of the $4^{th}$ internode of 'UGA 31' is longer than that of 'SI 98'. Stolons of 'UGA31' are larger in diameter than those of 'SI 98'. The unmowed culm height of 'UGA31' is much taller than the unmowed culm height of 'SI 98'. Both the upper and lower leaf surfaces of 'UGA 31' are slightly darker green than those of 'SI 98'.
6) The SSR banding patterns obtained when SSR marker C03996 is used with DNA from samples of 'UGA31' and 'SI 98' illustrate distinct differences between the two varieties. (See FIG. 5)

Comparisons are also shown in the tables to 'Sea Isle 1' (U.S. Plant Pat. No. 12,665) and 'Sea Isle 2000' (U.S. Plant Pat. No. 12,625). Table 11 comprises a comparison of a number of botanical features of these four varieties.

The salt tolerance of 'UGA 31' is similar to that of 'Sea Isle 1', 'Sea Isle 2000', and 'SI 98' (Tables 6 and 7).

With reference to FIG. 5, 'UGA 31' can be distinguished from 'SI 98', 'Sea Isle 1' and 'Sea Isle 2000' using SSRC03996, which amplifies a unique profile for 'UGA 31'. 'UGA 31' shares a fragment of about 110 base pairs with 'Sea Isle 2000'. This fragment can be used to distinguish this cultivar from 'SI 98'. 'UGA 31' shows two fragments of about 155 to 160 base pairs that distinguish these lines from 'Sea Isle 2000'.

All asexual reproductions of 'UGA 31' observed to date have been true to the original variety and remain true to type when asexually reproduced.

BRIEF DESCRIPTION OF THE PHOTOGRAPHS

Figure 1:
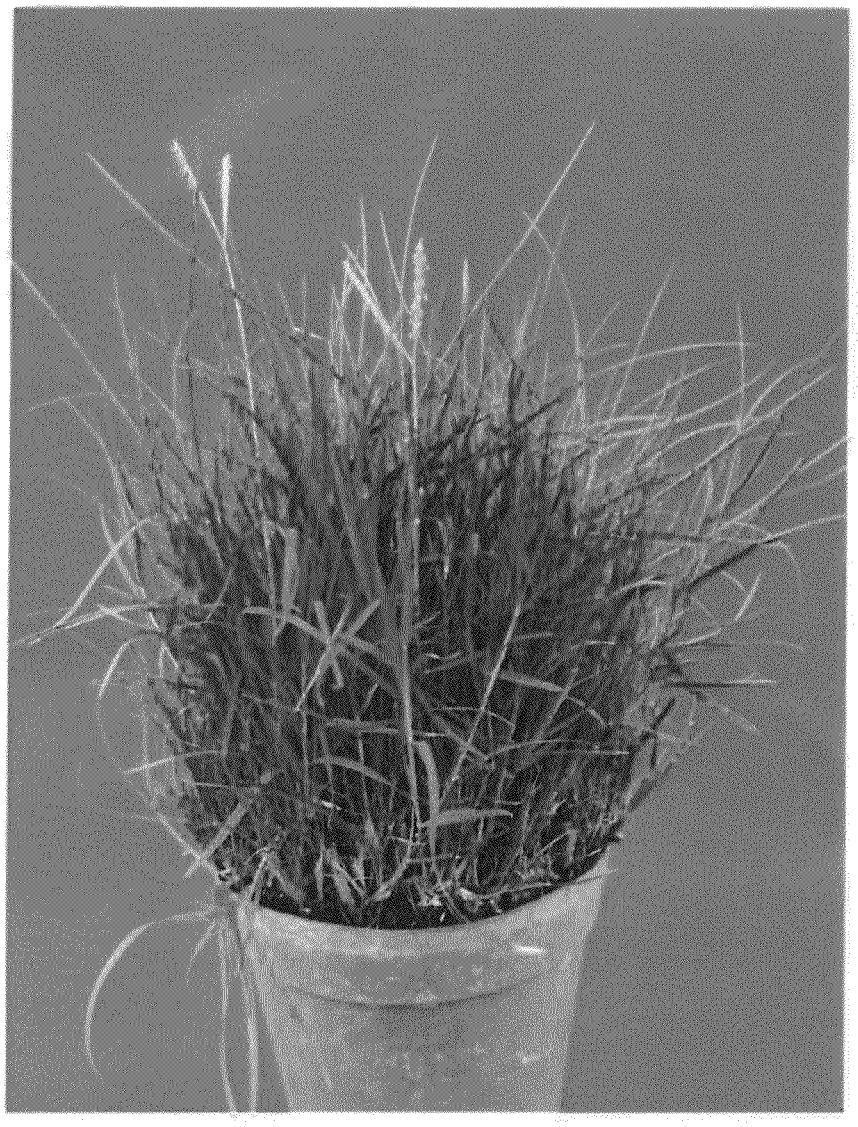
FIG. 1 shows a potted sample of 'UGA 31'.
Figure 2:
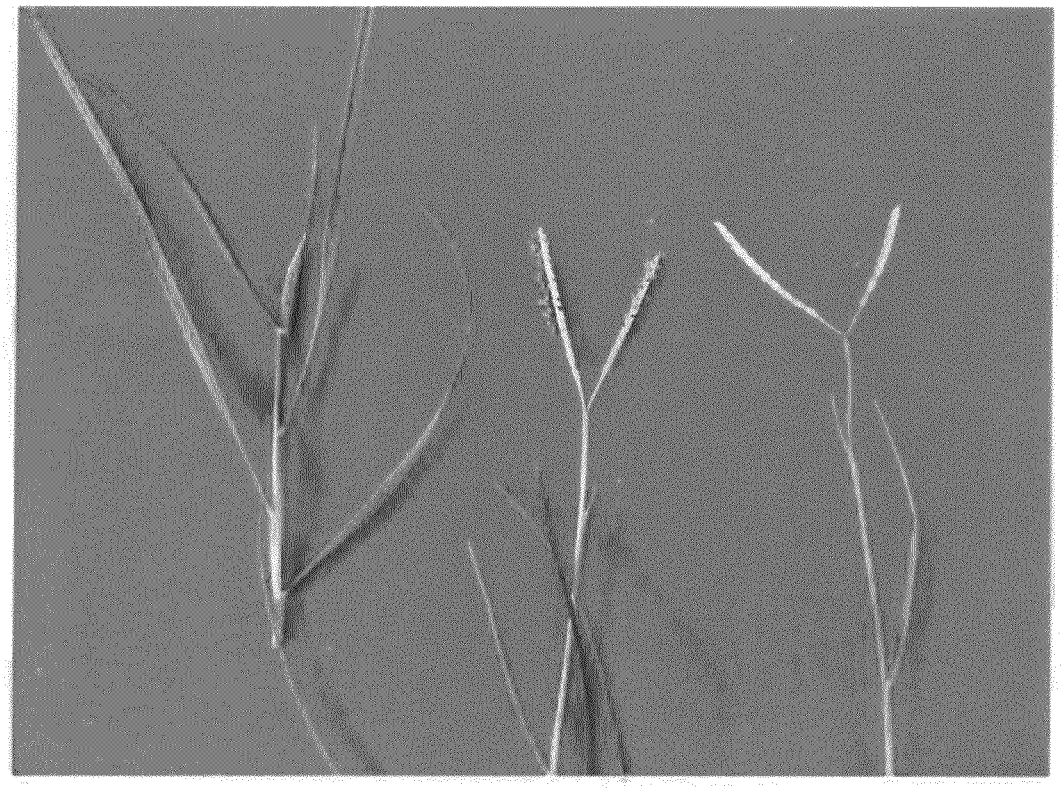
FIG. 2 shows the appearance of 'UGA 31' inflorescence prior to anthesis, at anthesis, and at maturity.
Figure 3:
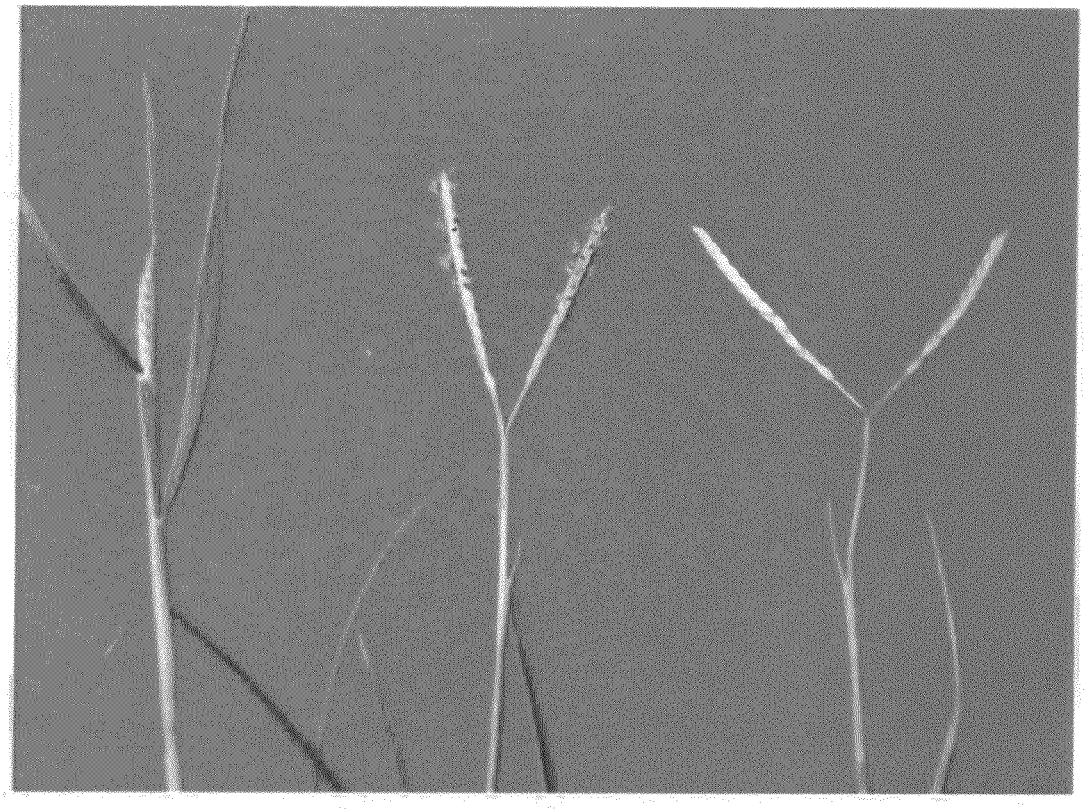
FIG. 3 is an enlargement of a portion of FIG. 2.
Figure 4:
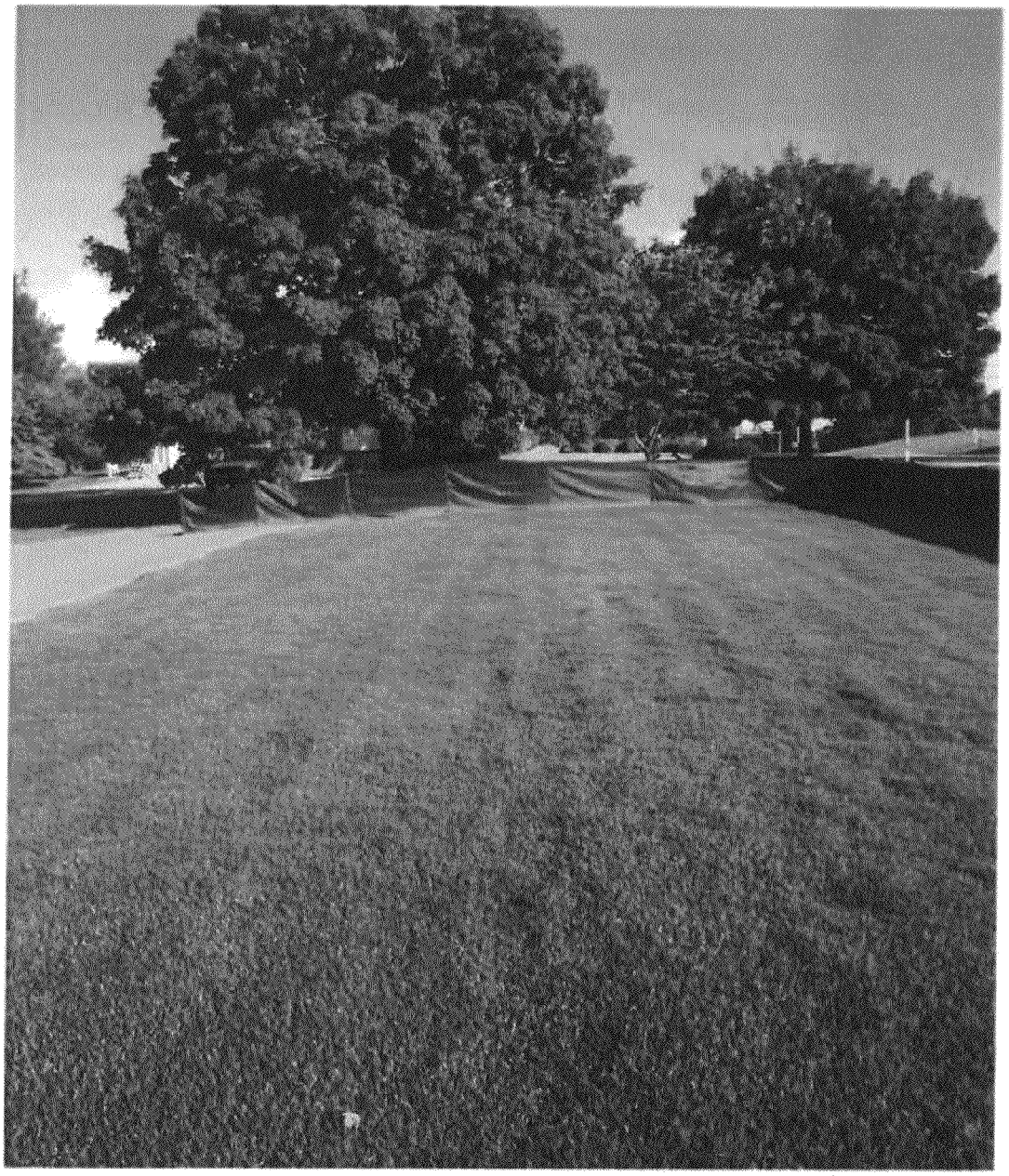
FIG. 4 illustrates a growing field plot of 'UGA 31'.
Figure 5:
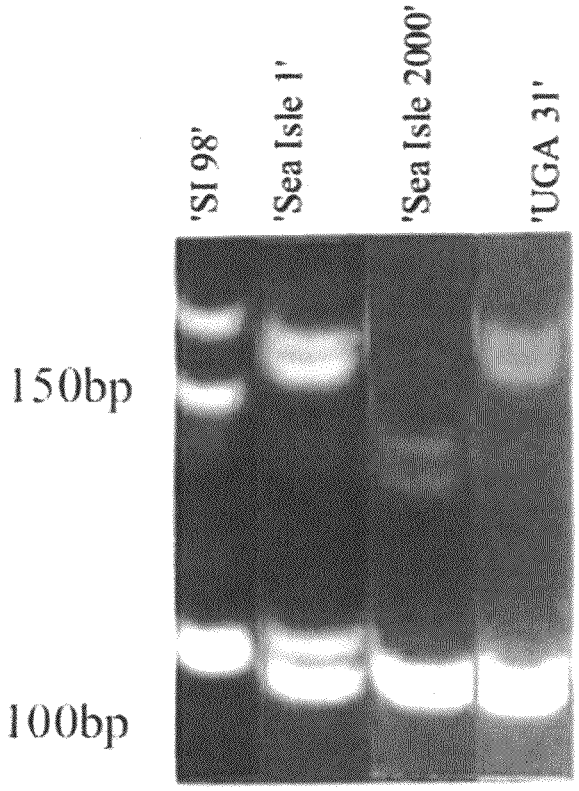

FIG. 5 compares the SSRC/03996 generated banding patterns obtained from DNA of 'UGA 31' to 'Sea Isle 1', 'Sea Isle 2000', and 'SI 98'.

DETAILED BOTANICAL DESCRIPTION

Certain characteristics of this variety, such as growth and color, may change with changing environmental conditions (e.g., light, temperature, moisture, nutrient availability, or other factors). Color descriptions and other terminology are used in accordance with their ordinary dictionary descriptions, unless the context clearly indicates otherwise. Color designations are made with reference to The Royal Horticultural Society (R.H.S.) Colour Chart.

The Plant

'UGA31' is a vigorous variety with upright growth habit. It is dense and spreads rapidly by producing large numbers of rhizomes and stolons.

The mean height of the unmown canopy (culm height) is 50.1 cm, with a seed head exsertion height of 37.4 cm.

Flowering Tillers

The mean length and diameter of the peduncle are respectively 8.3 mm and 0.5 mm.

The mean length of the longest spike is 31.6 mm and there are two spikes per inflorescence.

The mean length of the spike branch from the flag leaf is 8.4 mm and the length and width of the blade on the flag leaf are respectively 14.7 mm and 0.8 mm. The mean length of the sheath on the flag leaf is 40.6 mm.

The mean length and width of the blade of the $4^{th}$ leaf (the flag leaf is the $1^{st}$ leaf) are respectively 66.7 mm and 2.3 mm, and the mean length of the sheath on the $4^{th}$ leaf is 17.2 mm.

The mean length of the $4^{th}$ internode is 18.7 mm. The color of the upper leaf surface is Green 137 A and the lower leaf surface color is Green 137 A.

The anther color is Violet 86 A, and stigma color is Violet 83 A. Anthers are 1.0-1.5 mm long and the glumes are glabrous. Seeds are not produced in pure monostands due to self-incompatibility. Seeds are about 2.3 mm long and 1.0 mm wide and narrow in shape when produced by crossing with other widely diverse varieties of seashore *paspalum* plants.

Stolons

The mean length and diameter of the $4^{th}$ internode from the tip are 14.9 mm and 2.6 mm respectively.

The mean length and width of the $4^{th}$ leaf blade, at the $4^{th}$ node on stolon, are 6.5 mm and 1.4 mm respectively, with a leaf sheath that is 9.5 mm long.

The color of the stolon is Yellow-Green 146 B.

Disease Resistance

'UGA 31' is less susceptible to dollar spot than 'SI 98'. Dollar spot (*sclerotinia homoeocarpa*) is a fungal disease that attacks many turf grasses in the humid Southeast US when nitrogen levels are maintained at low levels under turf conditions.

Comparison Tables

Tables 1-11 that follow contain comparisons of botanical and other properties of 'UGA 31' with those of several other varieties.

TABLE 1

Performance comparison of seashore paspalum varieties under greens management (0.18-0.25 inch h.o.c.) at Griffin, Georgia 2008-2010[1]

| Variey | Grown-in Coverage (9 ratings) % cover | Turf Quality (15 ratings) 1-9 scale | Turf Color (9 ratings) 1-9 scale | Leaf Texture (2 ratings) 1-9 scale | Seed Heads (3 ratings) 1-9 scale | Fall Color (7 ratings) | Spring GreenUp (6 ratings) % | Dollar Spot (6 ratings) % | Pink Patch (3 ratings) % |
|---|---|---|---|---|---|---|---|---|---|
| 'Sea Isle 1' | 88.4 a | 7.1 cde | 7.2 de | 7.3 cd | 5.8 cde | 6.7 cd | 58.0 c | 2.6 d | 46.5 a |
| 'Sea Isle 2000' | 75.7 ab | 7.4 abc | 7.7 ab | 7.3 cd | 7.4 abc | 7.4 b | 50.5 cd | 3.2 d | 11.4 d |
| 'SI 98' | 88.4 ab | 6.8 ef | 7.2 de | 7.3 cd | 6.3 bcde | 7.6 b | 43.2 de | 17.1 a | 24.3 c |
| 'UGA 31' | 83.8 ab | 7.3 abc | 7.5 abcd | 7.5 bc | 6.6 bc | 7.7 ab | 61.9 bc | 5.1 cd | 9.7 d |

TABLE 2

Performance comparison of seashore paspalum varieties under fairway management (0.5 inches h.o.c.) at Tifton, Georgia 2007-2010.

| Variety | Grown-in Coverage (2 ratings) % cover | Turf Quality (12 ratings) 1-9 scale | Turf Color (4 ratings) 1-9 scale | Leaf Texture (1 rating) 1-9 scale | Turf Density (2 rating) | Seed Heads (2 ratings) 1-9 scale | Dollar Spot (6 ratings) % |
|---|---|---|---|---|---|---|---|
| 'Sea Isle l' | 87 a | 5.9 bc | 6.7 b | 6.8 bcd | 7.2 bc | 6.0 e | 2 c |
| 'Sea Isle 2000' | 77 a | 6.1 b | 7.3 a | 7.0 abc | 7.6 ab | 7.7 abc | 3 c |
| 'SI 98' | 87 a | 5.5 c | 6.5 b | 6.5 cd | 7.0 bc | 7.9 ab | 13 ab |
| 'UGA 31' | 80 a | 6.9 a | 7.7 a | 7.5 a | 8.2 a | 8.1 a | 1 c |

TABLE 3

Summary of 2007-2010 seashore paspalum test at Tifton, GA mowed at 0.5".

| | Turf Quality | | Green Cover | | Density | | Seedhead Density | |
|---|---|---|---|---|---|---|---|---|
| | 2009 Average | 2010 Average | 2009 Average | 2010 Average | 2009 Average | 2010 Average | Jun. 10, 2009 | Jul. 9, 2010 |
| No. Ratings | 9 | 6 | 9 | 7 | 9 | 6 | 1 | 1 |
| | visual rating[1] | | % coverage | | visual rating[1] | | no. per $M^2$ | |
| 'Sea Isle 1' | 5.6 cd | 4.5 cd | 85 a | 79 bcde | 6.0 de | 5.1 de | 1489 bc | 4801 a |
| 'Sea Isle 2000' | 6.5 b | 6.4 a | 85 a | 78 cde | 6.6 be | 6.3 ab | 219 d | 3520 ab |
| 'SI 98' | 4.6 f | 4.0 d | 84 a | 86 a | 5.0 g | 5.1 de | 151 d | 1338 c |
| 'UGA31' | 7.2 a[2] | 6.8 a | 83 ab | 84 abc | 7.1 a | 6.8 a | 319 d | 2479 bc |

TABLE 4

| 2009 seashore paspalum test at Tifton, GA mowed at 1.5" | | | | | |
|---|---|---|---|---|---|
| | Date | | | | |
| Variety | Jul. 2, 2009 | Jul. 21, 2009 | Sep. 5, 2009 | Oct. 7, 2009 | Nov. 18, 2009 |
| | | | Establishment % coverage | | |
| 'UGA 31' | 23 a | 53 a | 91 a | 99 a | 99 a |
| 'Sea Isle 1' | 8 a | 36 b | 83 b | 97 a | 97 a |

TABLE 5

| 2009 seashore paspalum test at Tifton, GA mowed at 1.5" | | | | | | |
|---|---|---|---|---|---|---|
| | Date | | | | | 2010 |
| Variety | May. 3, 2010 | Jun. 18, 2010 | Jul. 13, 2010 | Aug. 24, 2010 | Nov. 16, 2010 | Average |
| | | | Lawn Quality visual rating[1] | | | |
| 'UGA 31' | 6.3 a | 8.0 a | 7.3 a | 7.7 a | 5.0 a | 6.9 a |
| 'Sea Isle 1' | 6.0 a | 7.3 a | 6.3 a | 6.0 a | 3.3 a | 5.8 b |
| | | | Green Cover % coverage | | | |
| 'UGA 31' | 96 a | 97 a | 85 a | 88 a | 63 a | 86 a |
| 'Sea Isle 1' | 98 a | 97 a | 77 b | 71 b | 61 a | 81 b |
| | | | Density visual rating[1] | | | |
| 'UGA 31' | 6.3 a | 6.3 a | 7.7 a | 6.7 a | 5.7 a | 6.5 a |
| 'Sea Isle 1' | 6.0 a | 7.0 a | 7.0 a | 6.0 a | 3.3 b | 5.9 b |

TABLE 6

Response of seashore paspalum varieties after 60 days exposure to three levels of salt water in a replicated greenhouse experiment conducted in 2005.

| | Leaf Firing Salt Level (dS/m)[1] | | |
|---|---|---|---|
| Variety | 0.0 | 20.0 | 40.0 |
| | 0-9 scale (9 = excellent) | | |
| 'Sea Isle 1' | 8.2 a | 7.5 ab | 6.3 a |
| 'SI 98' | 8.7 a | 7.7 ab | 6.7 a |
| 'UGA 31' | 8.0 ab | 8.0 a | 6.0 ab |

TABLE 7

Response of seashore paspalum varieties after 60 days exposure to four levels of salt water in a replicated greenhouse experiment conducted in 2010.

| | Leaf Firing Salt Level (dS/m)[1] | | | |
|---|---|---|---|---|
| Variety | 0.0 | 15.0 | 30.0 | 45.0 |
| | 1-9 scale (9 = excellent) | | | |
| 'Sea Isle 1' | 8.2 abcde | 8.5 abc | 7.2 abcd | 3.6 ab |
| 'Sea Isle 2000' | 8.9 a | 8.7 abc | 8.2 ab | 2.1 bcde |
| 'SI 98' | 8.6 abc | 8.7 abc | 7.2 abcd | 2.1 bcde |
| 'UGA 31' | 8.7 ab | 9.0 a | 8.7 a | 3.2 abcd |

TABLE 8

Leaf firing response of seashore paspalum varieties to dry down in a replicated greenhouse lysimeter study conducted in 2007.[1]

| | Days from Initiation of Dry Down[2] | | | |
|---|---|---|---|---|
| Ecotype | 17 | 24 | 28 | 38 |
| | Leaf Firing (%) | | | |
| 'Sea Isle 1' | 14.00 abc | 17.00 bc | 9.33 d | 18.33 bc |
| 'Sea Isle 2000' | 11.33 bc | 10.67 bc | 8.33 d | 16.00 c |
| 'SI 98' | 11.67 bc | 34.33 ab | 31.67 abcd | 32.67 abc |
| 'UGA 31' | 3.33 c | 2.00 c | 3.00 d | 7.33 c |

TABLE 9

Summary of results of a turfgrass field drought study conducted under a Griffin, Georgia rainout shelter, Jul 29, 2008-Oct 28, 2008.

| | Average Across All Dates | | | |
|---|---|---|---|---|
| Grass | Leaf Firing % | NDVI Scale 1 = ideal | Turf Quality Scale 9 = ideal | Turf Color Scale 9 = ideal |
| 'Sea Isle 1' | 19.1 | 0.680 | 5.93 | 6.19 |
| 'Sea Isle 2000' | 16.1 | 0.704 | 6.15 | 6.62 |
| 'SI 98' | 41.7 | 0.619 | 4.49 | 4.78 |
| 'UGA 31' | 16.2 | 0.697 | 5.79 | 6.15 |

TABLE 10

Susceptibility of Paspalum cultivars to *Rhizoctonia solani* AG 2-2 LP (large patch) - Growth Chamber - May/June 2009.

| | % large patch | | | |
|---|---|---|---|---|
| Cultivar | May 21 | May 28 | June 4 | June 11 |
| 'Sea Isle 2000' | 6.4 b | 30.9 b | 45.3 b | 45.3 b |
| 'SI 98' | 2.9 b | 7.6 b | 10.5 c | 14.1 c |
| 'UGA 31' | 7.0 b[1] | 32.02 b | 45.3 b | 50.0 b |

TABLE 11

Comparison of botantical characteristics of four seashore paspalum cultivars.

| | 'Sea Isle 1' | 'Sea Isle 2000' | 'SI 98' | 'UGA 31' | LSD |
|---|---|---|---|---|---|
| Characteristics of Flowering Tillers | | | | | |
| Length of peduncle (mm) | | | | | |
| mean[1] | 8.3 a[1] | 10.4 a | 7.4 a | 8.3 a | N.S. |
| std dev | 5.8 | 6.7 | 4.5 | 1.8 | |
| Diameter of peduncle (mm) | | | | | |
| mean | 0.6 ab | 0.8 a | 0.7 a | 0.5 b | 0.2 |
| std dev | 0.2 | 0.2 | 0.2 | 0.2 | |
| Length of longest spike (mm) | | | | | |
| mean | 33.5 ab | 39.2 a | 29.7 b | 31.6 b | 5.9 |
| std dev | 5.7 | 9.8 | 4.4 | 2.5 | |
| Number of spikes per inflorescence | | | | | |
| mean | 2.0 a | 2.0 a | 2.0 a | 2.0 a | N.S. |
| std dev | 0.0 | 0.0 | 0.0 | 0.0 | |
| Maximum number of spikes per inflorescence | | | | | |
| mean | 2.0 a | 2.0 a | 2.0 a | 2.0 a | N.S. |
| std dev | 0.0 | 0.0 | 0.0 | 0.0 | |
| Length of spike branch from flag leaf (mm) | | | | | |
| mean | 7.5 a | 9.2 a | 7.0 a | 8.4 a | N.S. |
| std dev | 5.4 | 5.3 | 3.7 | 2.0 | |
| Number of florets per spike | | | | | |
| mean | 20.9 a | 22.3 a | 19.6 a | 21.6 a | N.S. |
| std dev | 5.1 | 6.8 | 2.7 | 2.1 | |
| Length of blade on flag leaf (mm) | | | | | |
| mean | 9.5 a | 16.8 a | 15.8 a | 14.7 a | N.S. |
| std dev | 3.7 | 7.7 | 11.3 | 5.3 | |
| Width of blade on flag leaf (mm) | | | | | |
| mean | 0.6 ab | 0.3 b | 0.8 a | 0.8 a | 0.4 |
| std dev | 0.4 | 0.1 | 0.5 | 0.5 | |
| Length/width ratio of flag leaf blade (mm) | | | | | |
| mean | 26.6 a | 50.9 a | 35.9 a | 28.8 a | N.S. |
| std dev | 25.6 | 18.9 | 47.8 | 31.2 | |

TABLE 11-continued

| Comparison of botantical characteristics of four seashore paspalum cultivars. | | | | | |
|---|---|---|---|---|---|
| | 'Sea Isle 1' | 'Sea Isle 2000' | 'SI 98' | 'UGA 31' | LSD |
| Length of sheath on flag leaf (mm) | | | | | |
| mean | 48.7 ab | 52.7 a | 40.6 b | 40.6 b | 10.7 |
| std dev | 10.1 | 17.2 | 10.3 | 3.0 | |
| Length of blade on 4th leaf (mm) | | | | | |
| mean | 80.7 a | 83.0 a | 71.9 a | 66.7 a | N.S. |
| std dev | 22.3 | 13.2 | 17.6 | 11.4 | |
| Width of blade on 4th leaf (mm) | | | | | |
| mean | 2.5 a | 1.7 b | 2.3 a | 2.3 a | 0.5 |
| std dev | 0.6 | 0.6 | 0.4 | 0.4 | |
| Length/width ratio of 4th leaf blade (mm) | . | | | | |
| mean | 33.6 b | 63.6 a | 31.4 b | 29.8 b | 22.9 |
| std dev | 8.1 | 50.2 | 6.7 | 6.8 | |
| Length of sheath on 4th leaf (mm) | | | | | |
| mean | 21.6 a | 24.3 a | 14.6 b | 17.2 b | 3.7 |
| std dev | 6.4 | 1.5 | 2.5 | 3.8 | |
| Length of 4th internode (mm) | | | | | |
| mean | 18.8 a | 21.4 a | 10.6 b | 18.7 a | 3.9 |
| std dev | 3.5 | 3.5 | 2.1 | 6.5 | |
| Characteristics of Stolons | | | | | |
| Length of 4th internode (mm) | | | | | |
| mean | 14.1 a | 12.3 a | 10.1 a | 14.9 a | N.S. |
| std dev | 4.7 | 5.7 | 3.6 | 4.8 | |
| Diameter of 4th internode (mm) | | | | | |
| mean | 2.8 a | 2.0 b | 1.9 b | 2.6 a | 0.5 |
| std dev | 0.6 | 0.7 | 0.3 | 0.5 | |
| Length of 4th leaf blade (mm) | | | | | |
| mean | 17.9 a | 18.9 a | 11.4 b | 6.5 b | 5.0 |
| std dev | 7.6 | 3.8 | 5.0 | 3.1 | |
| Width of 4th leaf blade (mm) | | | | | |
| mean | 2.2 ab | 2.7 a | 1.6 bc | 1.4 c | 0.7 |
| std dev | 0.9 | 0.7 | 0.6 | 0.6 | |
| Length/width ratio of 4th leaf blade (mm) | | | | | |
| mean | 9.1 a | 7.6 ab | 7.5 ab | 5.0 b | 3.0 |
| std dev | 3.3 | 3.0 | 3.9 | 2.3 | |
| Length of leaf sheath on 4th node (mm) | | | | | |
| mean | 11.6 a | 10.0 a | 9.6 a | 9.5 a | N.S. |
| std dev | 2.3 | 3.9 | 2.1 | 1.6 | |

TABLE 11-continued

Comparison of botantical characteristics of four seashore paspalum cultivars.

| | 'Sea Isle 1' | 'Sea Isle 2000' | 'SI 98' | 'UGA 31' | LSD |
|---|---|---|---|---|---|
| Other Characteristics | | | | | |
| Culm height (cm) | | | | | |
| mean | 43.9 a | 28.9 b | 23.1 b | 50.1 a | 8.9 |
| std dev | 15.1 | 5.2 | 4.1 | 9.7 | |
| Seed head height (cm) | | | | | |
| mean | 39.0 | 36.4 | 27.6 | 37.4 | N.S. |
| std dev | 16.7 | 6.0 | 8.2 | 6.1 | |
| Color of upper leaf surface[2] | 137 B | 137 B | 137 B | 137 A | |
| Color of lower leaf surface | 137 A | 137 A | 137 C | 137 A | |
| Stolon Color | 146 A | 146 C | 146 B | 146 B | |
| Anther Color | 86 A | 86 A | 86 A | 86 A | |
| Stigma Color | 83 A | 83 A | 83 A | 83 A | |

[1]Means within a row followed by the same letter are not considered statistically different according to Fisher's protected LSD at $\alpha = 0.05$.
[2]Based on color codes of The Royal Horticultural Society Colour Chart.

We claim:

1. A new and distinct cultivar of seashore *paspalum* plant named 'UGA 31', substantially as herein illustrated and described.

* * * * *

SSRC03996